(12) United States Patent
Agarwal et al.

(10) Patent No.: US 9,804,331 B2
(45) Date of Patent: Oct. 31, 2017

(54) PRE-ASSEMBLED WHISPERING GALLERY MODE RESONANCE SENSORS, FOR USE AS DIP SENSORS OR VAPOR SENSORS, FOR EXAMPLE, AND METHODS FOR MAKING SUCH SENSORS

(71) Applicants: Monica Agarwal, Troy, NY (US); Natalie Huiyi Luo, Brooklyn, NY (US); Iwao Teraoka, Rye, NY (US)

(72) Inventors: Monica Agarwal, Troy, NY (US); Natalie Huiyi Luo, Brooklyn, NY (US); Iwao Teraoka, Rye, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 14/823,840

(22) Filed: Aug. 11, 2015

(65) Prior Publication Data
US 2016/0070067 A1    Mar. 10, 2016

Related U.S. Application Data

(60) Provisional application No. 62/047,291, filed on Sep. 8, 2014, provisional application No. 62/099,391, filed on Jan. 2, 2015.

(51) Int. Cl.
*G02B 6/293* (2006.01)
*G01N 21/77* (2006.01)

(52) U.S. Cl.
CPC ..... *G02B 6/29341* (2013.01); *G01N 21/7746* (2013.01)

(58) Field of Classification Search
CPC .............. G02B 6/29341; G02B 6/29338
See application file for complete search history.

(56) References Cited

U.S. PATENT DOCUMENTS

2007/0269901 A1* 11/2007 Armani .............. G01N 21/7746
436/172

* cited by examiner

*Primary Examiner* — Jerry Rahll
(74) *Attorney, Agent, or Firm* — John C. Pokotylo

(57) ABSTRACT

A robust sensor, suitable for dipping into fluid wells, includes (a) a stem; (b) a whispering gallery mode ("WGM") resonator mechanically supported by the stem; and (c) feed and pickup optical fibers optically coupled with the WGM resonator and mechanically coupled with the stem, thereby defining a stem-resonator-fiber assembly, wherein a portion of the stem-resonator-fiber assembly including the WGM resonator can fit within an imaginary cylinder having a diameter of 7 mm (or 2 mm, or even 1 mm). Such a whispering gallery mode ("WGM") dip sensor, including (1) a stem, (2) a WGM resonator, and (3) feed and pickup optical fibers, may be made by (a) fabricating the WGM resonator and the stem from an optical fiber; (b) fabricating tapers on the feed and pickup fibers; (c) positioning tapers of the feed and pickup fibers relative to the WGM resonator such that an optical coupling between the tapers and the WGM resonator is established; and (d) mechanically coupling the stem with the feed and pickup fibers.

21 Claims, 17 Drawing Sheets

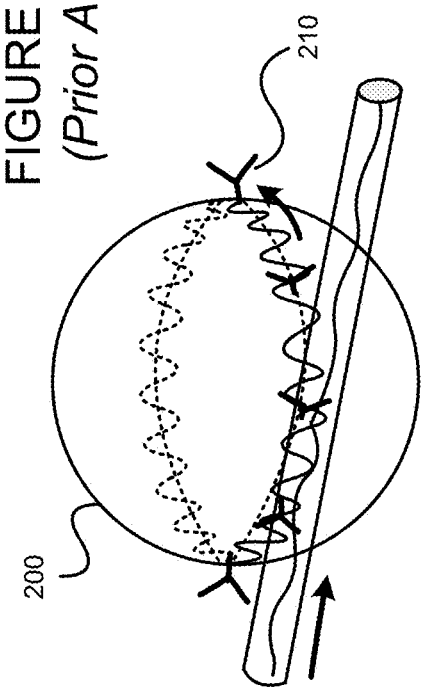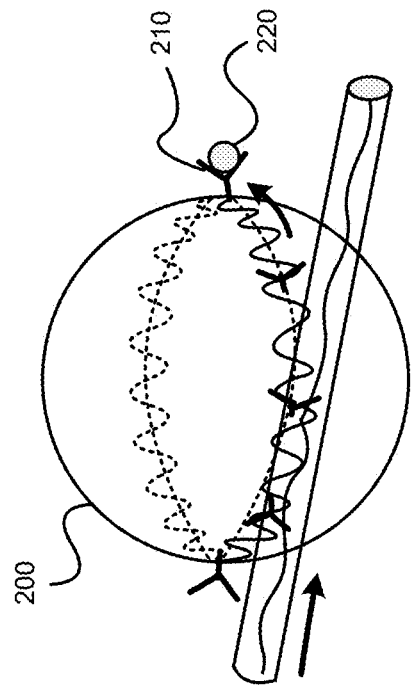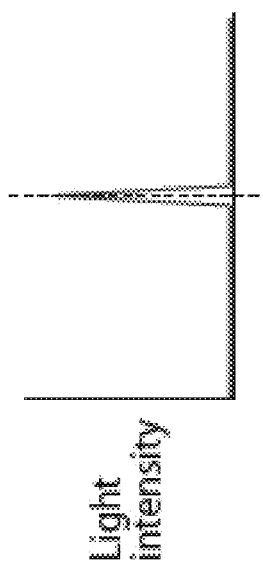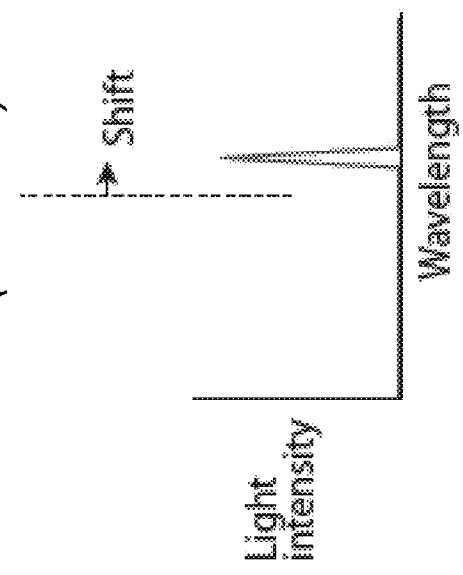

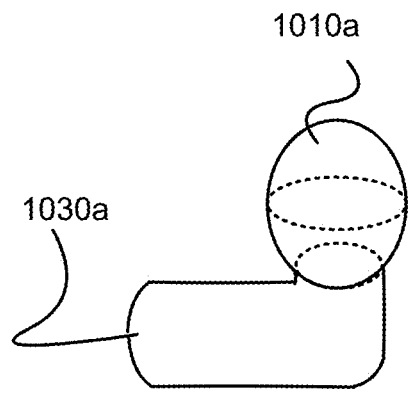
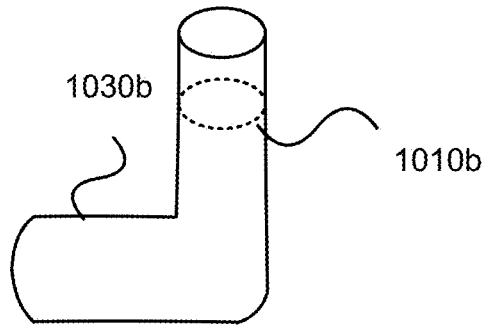
FIGURE 10A     FIGURE 10B
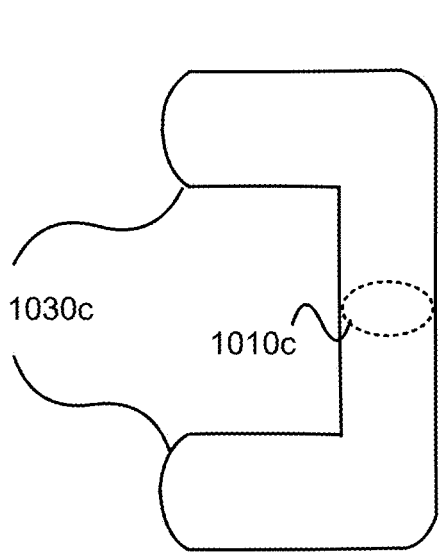
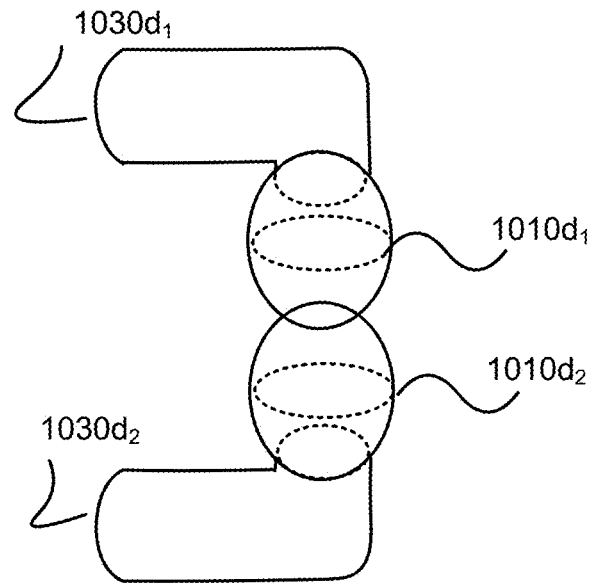
FIGURE 10C     FIGURE 10D

PRE-ASSEMBLED WHISPERING GALLERY MODE RESONANCE SENSORS, FOR USE AS DIP SENSORS OR VAPOR SENSORS, FOR EXAMPLE, AND METHODS FOR MAKING SUCH SENSORS

§0. RELATED APPLICATIONS

This application claims benefit to both (1) U.S. Provisional Application Ser. No. 62/047,291, "PRE-ASSEMBLED WHISPERING GALLERY MODE RESONANCE SENSORS, FOR USE AS DIP SENSORS OR VAPOR SENSORS, FOR EXAMPLE, AND METHODS FOR MAKING SUCH SENSORS," filed on Sep. 25, 2014 and listing Iwao Teraoka and Monica Agarwal as the inventors (referred to as "the '291 provisional" and incorporated herein by reference), and (2) U.S. Provisional Application Ser. No. 62/099,391, titled "PRE-ASSEMBLED WHISPERING GALLERY MODE RESONANCE SENSORS, FOR USE AS DIP SENSORS OR VAPOR SENSORS, FOR EXAMPLE, AND METHODS FOR MAKING SUCH SENSORS," filed on Jan. 2, 2015 and listing Iwao Teraoka and Monica Agarwal as the inventors (referred to as "the '391 provisional" and incorporated herein by reference). The scope of the present invention is not limited to any requirements of the specific embodiments described in '291 and '391 provisionals.

§1. FEDERAL FUNDING/GOVERNMENT RIGHTS IN THE INVENTION

This invention was made with Government support and the Government may have certain rights in the invention as provided for by grant number 1040015 awarded by the National Science Foundation.

§2. BACKGROUND OF THE INVENTION

§2.1 Field of the Invention

The present invention concerns whispering gallery mode ("WGM") sensors that can detect the presence of, identify the composition of, and/or measure an amount or concentration of substances (referred to generally as "target entities," "target analytes," or simply "targets"), such as chemical or biological entities. The present invention also concerns methods and apparatus to make, and/or use such WGM sensors.

§2.2 Background Information

There exists an ongoing need for sensors for detecting various targets such as, for example, infectious agents (e.g., viruses, bacteria, etc.), toxins, small amounts of proteins, DNA, RNA, etc. Similarly, there exists an ongoing need for sensors for measuring DNA hybridization, protein adsorption, biomolecular mass, etc. Dip sensors would be convenient for interfacing with fluid samples. However, they are not available for all sensing methods. If available, the sensitivity is often compromised compared with non-dip sensors.

Nearly all biosensing methods that claim a high sensitivity, such as surface plasmon resonance and quartz crystal microbalance for example, use a microfluidic system for (1) introducing a sample solution for analysis and (2) rinsing the sensor. Unfortunately, this is much more complicated compared with introducing a dip sensor into a sample solution and subsequently rinsing the sensor in a target-free buffer. Such known high sensitivity biosensing methods have not been used as dip sensors because, in each case, their sensor head assembly is too large to match the size of the wells in well plates.

The need for fast and early detection of pathogens (e.g. viruses) and the antibodies that are generated as a biological response has led to the development of ultra-sensitive label-free biosensors that can detect individual bio-nanoparticles in aqueous solution. One known device used to detect the presence of small particles is a microsphere sensor coupled with an optical waveguide (e.g., an optical fiber with an eroded section), one end of which is optically coupled with a light source and the other end with a light detector. Whispering gallery modes ("WGM's") of the light circulating within the microsphere can be observed in optical signals detected at the detector. Examples of such WGM sensors are described in U.S. Pat. No. 7,491,491 (referred to as "the '491 patent" and incorporated herein by reference).

WGM sensors rely on the inherent sensitivity of the WGM resonances within the resonator to changes in the external environment to provide a sensitive detection mechanism. When light travels within a transparent medium of a circular cross section on a track near the surface of the medium by total internal reflection, the light superimposes onto itself after one cycle. If the cycle contains an integral number of waves, the superposition is constructive, and the amplitude of light multiplies by hundreds or thousands. (See, e.g., 100 of FIG. 1.) This strong mode of light propagation is observed as a narrow-line resonance called a "whispering gallery mode" or "WGM".

The wavelength is sensitive to the temperature, as the refractive index of the resonator changes with temperature. The resonance wavelength is also sensitive to the refractive index of the immediate neighborhood of the surface. Target entities selectively captured (e.g., adsorbed) by target receptors onto the surface of the microsphere (or some other resonator) may shift the whispering gallery modes. As can be appreciated by comparing FIGS. 2A and 2B with FIGS. 2C and 2D, a WGM sensor 200 utilizes the shift of resonance wavelength (Compare FIGS. 2A and 2C.) when a receptor 220 binds to a ligand 210 immobilized on the resonator's surface (Compare FIGS. 2B and 2D.). Since an extremely small shift can be easily observed, the resonator has a high sensitivity to the temperature and the composition of the surrounding medium.

After being proposed more than ten years ago, there has been intensive research on WGM sensors. WGM sensors have emerged as an important optical tool for detecting and analyzing trace quantities of biological materials. WGM sensors have been employed in a host of applications including the detection of virus and bacteria, measurement of DNA hybridization and protein adsorption, and biomolecular mass determination.

U.S. Patent Application Publication No. 2004-0137478 (referred to as "the '478 publication" and incorporated herein by reference), titled "ENHANCING THE SENSITIVITY OF A MICROSPHERE SENSOR," discusses increasing the sensitivity of WGM sensors. More specifically, the '478 publication describes creating a band (e.g., a narrow band) of target receptors such that the target receptors are substantially limited to a highly sensitive region near the equator of a microsphere (also referred to as the "equator region"). The '478 publication discusses fabricating microsphere sensors having target receptors substantially only at a sensitive equator region of a microsphere's surface.

U.S. Pat. No. 8,642,111 (referred to as "the '111 patent" and incorporated herein by reference), titled "FUNCTIONALIZING A SENSING RIBBON ON A WHISPERING GALLERY MODE MICRORESONATOR USING LIGHT FORCE TO FABRICATE A WHISPERING GALLERY MODE SENSOR," discusses using light force to fabricate WGM sensors including microresonators having target receptors selectively and substantially provided at only equator region (or mode volume) of the microresonators. More specifically, the '363 publication discusses fabricating microsphere sensors for determining the presence or concentration of a target entity in a medium.

U.S. Pat. No. 8,493,560 (referred to as "the '560 patent" and incorporated herein by reference), titled "PLASMONIC ENHANCEMENT OF A WHISPERING-GALLERY-MODE BIOSENSORS," describes sensors for determining the presence or concentration of a target entity in a medium. Such sensors may include (a) an optical waveguide; (b) a microresonator optically coupled with the optical waveguide such that light within the optical waveguide induces a resonant mode within the microresonator at an equator region (or a mode volume); and (c) at least one plasmonic nanoparticle adsorbed onto a surface area of the microresonator within the equator region (or the mode volume) such that light inducing a resonant mode within the microresonator also causes a plasmonic resonance in the at least one plasmonic nanoparticle. Detection methods for using such sensors are also described. Finally, methods, involving the use of carousel forces, for fabricating such sensors are also described.

U.S. Pat. No. 8,886,270 (referred to as "the '270 patent" and incorporated herein by reference), titled "SYRINGE-BASED WHISPERING GALLERY MODE MICRORESONATOR MICROFLUIDIC BIOCHEM SENSOR," describes a syringe-based whispering gallery mode sensor having a syringe, the syringe including an assembly provided its needle, the assembly including (1) an optical carrier having a reflective distal end, and (2) at least one resonator coupled with the optical carrier. This sensor may be provided in a system including a light source, a light detector, and a data analysis component. A method for determining the presence or concentration of a target substance in body fluid may be performed using such a system.

As shown in FIG. 3, past studies of WGM biosensor and chemosensor used, for example, a fluidic device 300 that holds a fluid permeating the resonator and a taper (to feed light into the resonator). When a fluid containing target molecules is introduced into the surroundings, the resonance wavelength shifts. (Recall FIGS. 2A-2D.)

In the fluidic device, the position of the taper relative to the resonator is carefully optimized by a three-dimensional positioner. Unfortunately, however, common bench top noises can easily disturb the coupling and extinguish the resonance. To reestablish resonance, adjustment is needed to reposition the taper relative to the resonator. The requirement of frequent optical repositioning has been a source of frustration for biologists, clinical scientists, biochemists and chemists who want to study and/or exploit WGM sensors. Furthermore, such repositioning can cause scratches on the resonator's surface, and such scratches can make the resonator useless in a WGM sensor. Consequently, the past studies have been mainly conducted, nearly exclusively, in physics, bioengineering, and electrical engineering laboratories.

Therefore, it would be useful to provide a more robust WGM sensor. A ready-to-use, mechanically robust, pre-assembled sensor head that does not need optical alignment would be especially useful. It would be useful if such a WGM sensor could be dipped into, and removed from, wells of known well plates, without losing or disturbing its resonance.

§3. SUMMARY OF THE INVENTION

An example apparatus consistent with the present invention includes (a) a stem; (b) a whispering gallery mode ("WGM") resonator mechanically supported by the stem; and (c) feed and pickup optical fibers optically coupled with the WGM resonator and mechanically coupled with the stem, thereby defining a stem-resonator-fiber assembly, wherein a portion of the stem-resonator-fiber assembly including the WGM resonator can fit within an imaginary cylinder having a diameter of 7 mm. In some example embodiments consistent with the present invention, the portion of the stem-resonator-fiber assembly including the WGM resonator can fit within an imaginary cylinder having a diameter of 2 mm, and still others can fit within an imaginary cylinder having a diameter of 1 mm.

In some example apparatus consistent with the present invention, the mechanical support of the WGM resonator by the stem and the mechanical coupling of the feed and pickup optical fibers with the stem is such that the resonator can be dipped into and removed from a liquid while maintaining a WGM resonance in the WGM resonator.

In some example apparatus consistent with the present invention, the stem includes a bend of approximately 90 degrees.

In some example apparatus consistent with the present invention, the feed and pickup optical fibers physically contact the WGM resonator, and in some example apparatus, the feed and pickup optical fibers are mechanically coupled with the stem via a spacer. In some example embodiments, the spacer is defined by an outer wall of an inner capillary.

Other embodiments consistent with the present invention may further include an outer capillary defining an inner volume accommodating the WGM resonator, and/or a thermistor arranged proximal to the WGM resonator. In some example embodiments, an air passage is defined from a first open end of the outer capillary to an outlet in the outer capillary. In some such embodiments, the air passage is defined by a hollow needle.

In some example embodiments consistent with the present invention, each of the feed and pickup optical fibers includes a conical distal end mechanically and optically coupled with the WGM resonator.

In some example embodiments consistent with the present invention, the WGM sensor is a sphere, while in other example embodiments, the WGM sensor is a cylinder.

In some example embodiments consistent with the present invention, the stem has a diameter of at least 30 µm, while in other example embodiments, the stem has a diameter of from 300 µm to 400 µm, and in yet other example embodiments, the stem has a diameter of from 30 µm to 1 mm.

Some example methods, consistent with the present invention, of fabricating a whispering gallery mode ("WGM") dip sensor, including (1) a stem, (2) a WGM resonator, and (3) feed and pickup optical fibers, include (a) fabricating the WGM resonator and the stem from an optical fiber; (b) fabricating tapers on the feed and pickup fibers; (c) positioning tapers of the feed and pickup fibers relative to the WGM resonator such that an optical coupling between the tapers and the WGM resonator is established; and (d) mechanically coupling the stem with the feed and pickup fibers. In some such example methods, the act of fabricating the WGM resonator and the stem from an optical fiber includes (1) bending an optical fiber approximately 90° with a localized heat source to form a bent arm, (2) cutting the bent arm to an desired length, and (3) forming a sphere at a tip of the bent arm using a localized heat source. In some such example methods, the act of mechanically coupling the stem with the feed and pickup fibers includes (1) mechanically fixing the stem to a spacer, (2) mounting tapers of the feed and pickup fibers on a horizontal stage that can be moved in XYZ directions, (3) moving the tapers may so that their tips touch the WGM resonator, and (4) mechanically fixing the feed and pickup fibers to the spacer.

§4. BRIEF DESCRIPTION OF THE DRAWINGS

FIGS. 2A-2D illustrate how a WGM sensor utilizes a shift of resonance wavelength that occurs when a target binds to a receptor on the surface of the resonator.

FIGS. 10A-10D illustrate alternative stem-resonator assemblies that may be used in a WGM sensor consistent with the present invention.

§5. DETAILED DESCRIPTION

§5.1 Example Sensor

Figure 1:
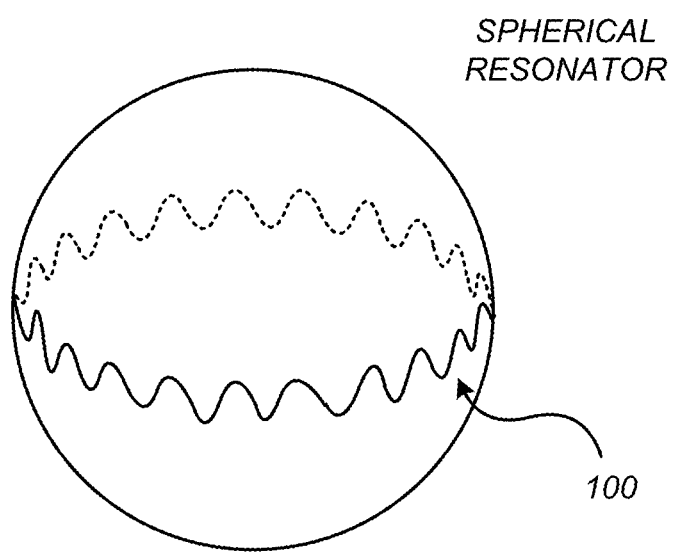
FIG. 1 illustrates that when light travels within a transparent medium of a circular cross section on a track near the surface of the medium by total internal reflection, the light superimposes onto itself after one cycle.
Figure 3:
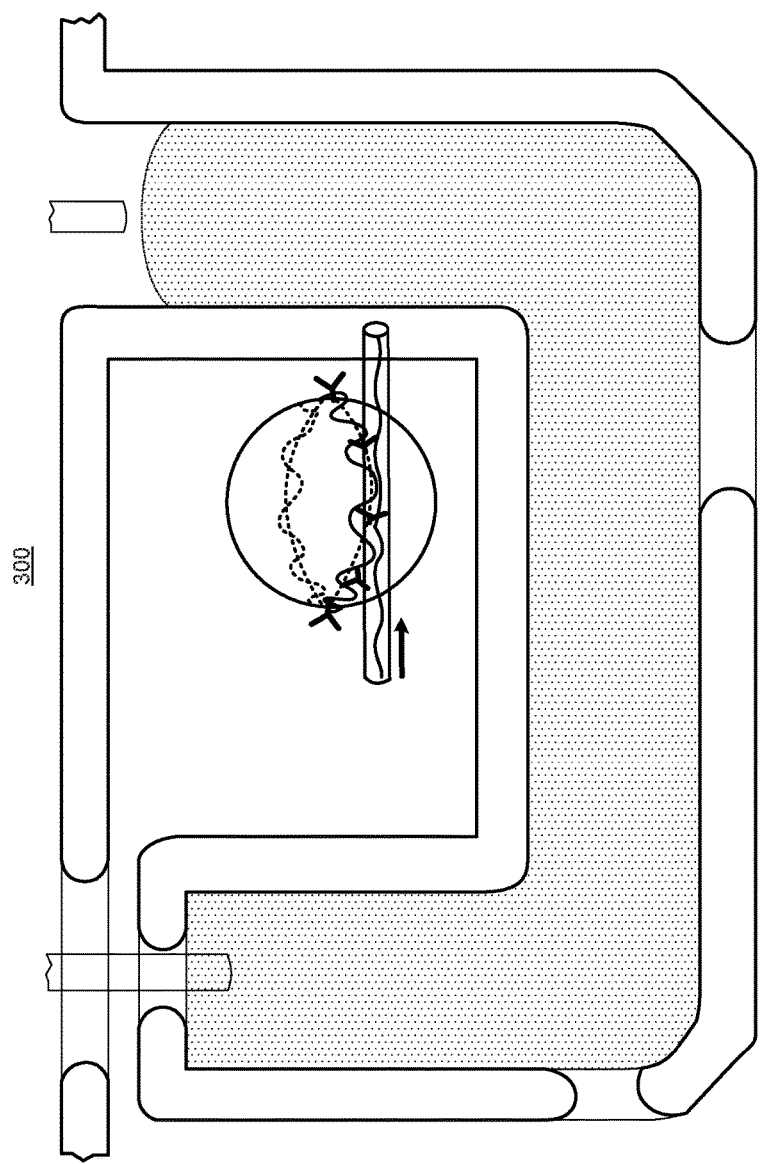
FIG. 3 illustrates how past studies of WGM biosensors and chemosensors used a fluidic device that holds a fluid permeating a resonator.
Figure 4:
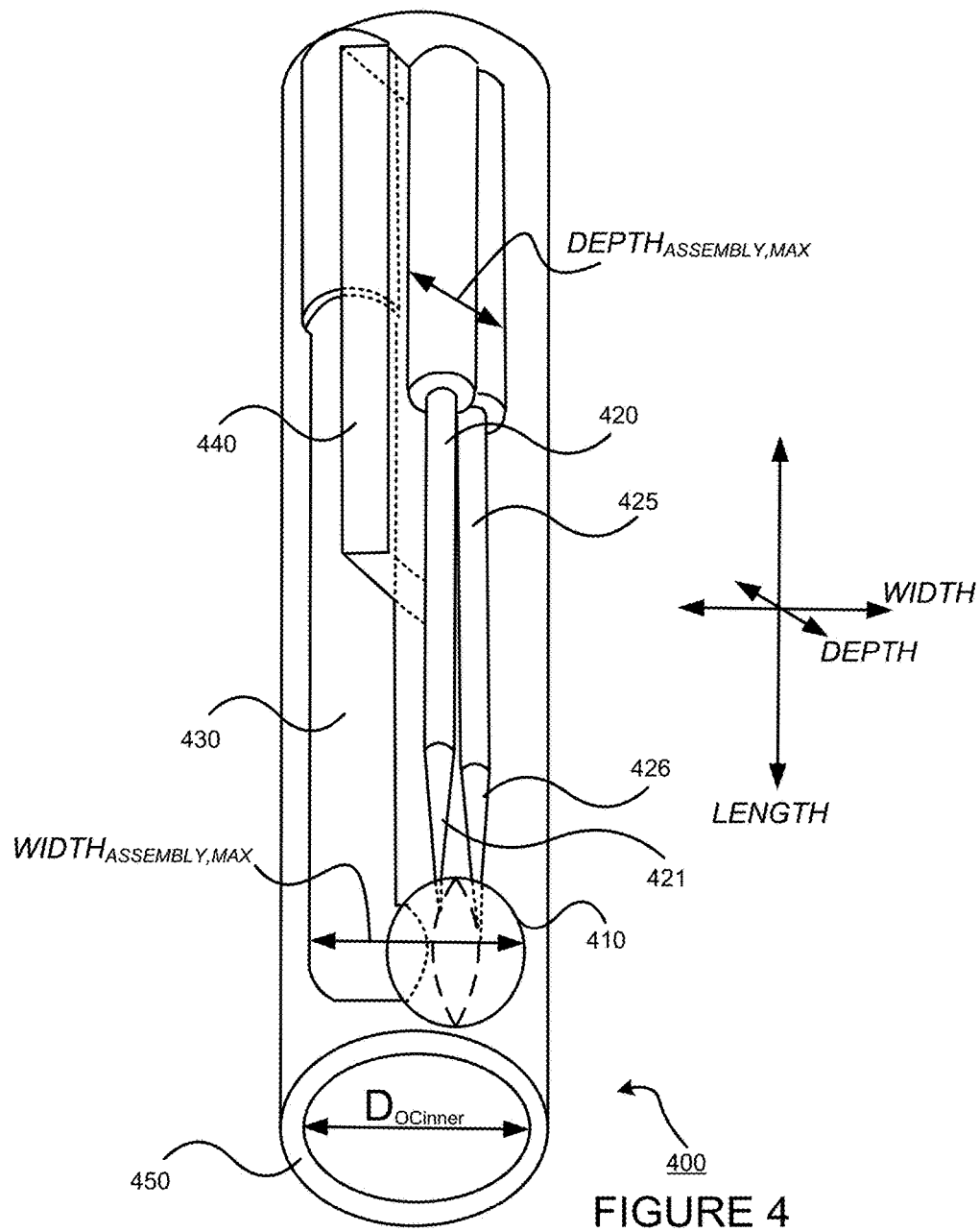
FIG. 4 is a perspective, semi-transparent, view of an example WGM dip sensor consistent with the present invention.

FIG. 4 is a perspective, semi-transparent, view of an example WGM sensor head 400 (or simply referred to as a "WGM sensor" or a "sensor") consistent with the present invention. As is the case with some conventional WGM sensors, the example sensor includes a resonator 410, a feed fiber 420 and a pickup fiber 425. (Note that most conventional WGM sensors use a single through taper, which both feeds light into the resonator, and picks up light from the resonator.) However, the example WGM sensor of FIG. 4 further includes a stem 430, a spacer 440, and an outer capillary 450 (or outer tube).

Each of the two fibers 420/425 is honed to a cone 421/426. The tips of the cones 421/426 touch the resonator 410. The feed fiber 420 feeds light (e.g., sourced from a laser, not shown) into the resonator 410, and the pick-up fiber 425 picks up the light in the resonator 410 (e.g., for measurement by a detector, not shown).

The resonator 410 is attached to a stem 430 and has a circular cross section. In the example embodiment illustrated, the resonator 410 is a microsphere. The axis of the resonator 410 normal to its circular cross section defines an angle of about 90° with the stem. Other angles (for example, a range of 70-110 degrees, and more preferably a range of 80-100 degrees) are possible, provided that the stem 430 does not interfere with the optical resonance at the equator (or circular cross section) of the resonator 410.

In the example WGM sensor 400, the stem 430 and the two fibers 420/425 are substantially parallel to each other, though this is not strictly necessary. The relative positions of the stem 430 and the two fibers 420/425 are defined by a spacer 440. Although the spacer 440 is illustrated as a parallel-piped slab, other spacers (e.g., a wall of a smaller glass capillary) are possible. In the example WGM sensor 400, the two fibers 420/425 and the stem 430 are glued to the spacer 440.

Figure 5:
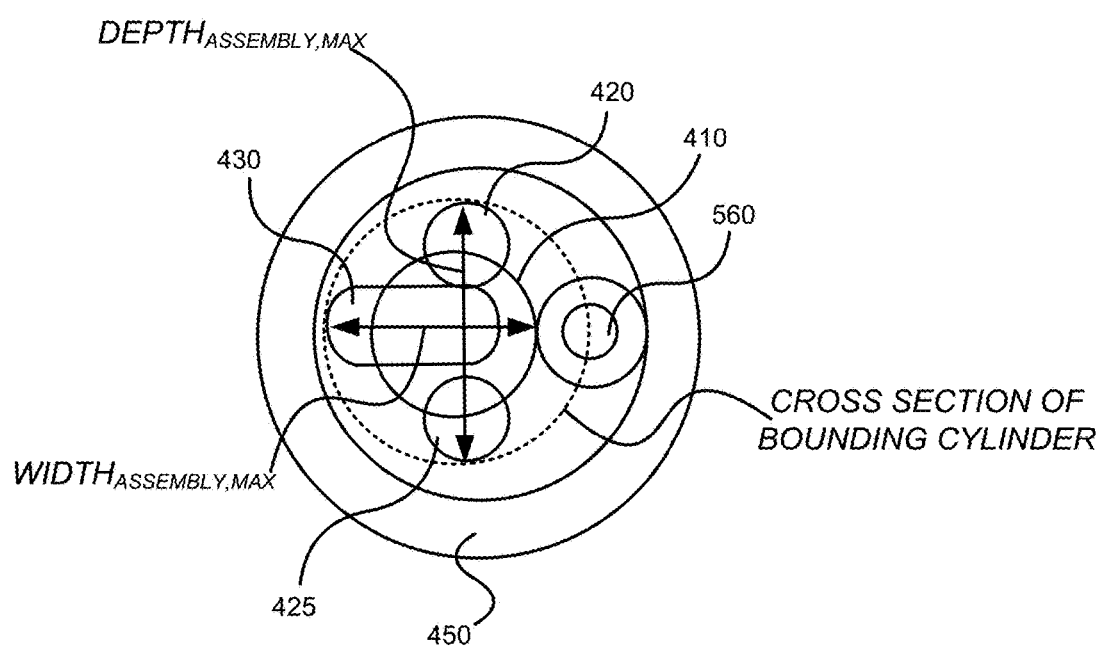
FIG. 5 is cross-sectional plan view of an example WGM dip sensor consistent with the present invention.

Referring to FIG. 4, in the example WGM sensor 400, the stem-resonator-fiber assembly has a length, a width and a depth, each orthogonal to the other. Referring to both FIGS. 4 and 5, a maximum width of the stem-resonator-fiber assembly ($WIDTH_{ASSEMBLY,MAX}$) and a maximum depth of the stem-resonator-fiber assembly ($DEPTH_{ASSEMBLY,MAX}$) can be fit within an imaginary cylinder, the cross section of which is illustrated in FIG. 5. For example, in the example WGM sensor 400 of FIG. 4, the diameter of the imaginary cylinder is not larger than the inner diameter of the outer capillary ($D_{OCinner}$). More generally, any combination of cross sections of the stem-resonator-fiber assembly orthogonal to the length directions (or at least a combination of any such cross sections at portions of the stem-resonator-fiber assembly to be dipped into a sample well) can fit within the imaginary cylinder. For example, a portion of the stem-resonator-fiber assembly including the WGM resonator 410 can fit within the imaginary cylinder. In some example embodiments consistent with the present invention, the diameter of the imaginary cylinder is 7 mm. In other example embodiments consistent with the present invention, the diameter of the imaginary cylinder is 2 mm. In still other example embodiments consistent with the present invention, the diameter of the imaginary cylinder is 1 mm. Such embodiments can advantageously fit within a well of standard 6-well, 12-well, 24-well, and/or 96-well plates. Indeed, a bundle including more than one stem-resonator-fiber assembly consistent with the present invention can be dipped into a well of a standard well plate.

In the example WGM sensor 400, the outer capillary 450 (or outer tube) encloses (at least) the resonator 410 and the fiber tips. The resonator 410 and the fiber tips may be enclosed in the outer capillary 450 using a glue. The outer capillary 450 makes the WGM sensor 400 more mechanically robust and protects the resonator 410 and the cones 421/426 of the two fibers 420/425. When the bottom of the WGM sensor 400 is dipped into a liquid to be analyzed, capillary rise will cause the liquid to fill the interior of the outer capillary 450 (or outer tube). The liquid within the capillary advantageously reduces disturbances in the resonator-cone coupling when the WGM sensor 400 is lifted from the liquid. The outer capillary 450 can be made of glass, plastic, metal, and the like. The inner surface of the outer capillary 450 can be chemically modified to retain a polar or a nonpolar liquid. For example, silane coupling agents can be used for this purpose. They will turn the glass surface to hydrophilic, hydrophobic, aromatic, aliphatic, etc. The modification of the outer capillary 450 should be done prior to attaching it to the resonator-fiber assembly.

Referring to FIG. 5, the capillary rise of the liquid into the outer capillary 450 (or outer tube) requires an air passage within the capillary, so that air within the capillary 450 can be displaced by the liquid. To provide an air passage, the glue should not completely fill the space within the outer capillary to block the air flow. As shown in the cross section of FIG. 5, one way to provide an air passage is to insert a hollow needle 560, the cross section of which is illustrated in FIG. 5, before filling the gap with glue. Further, the needle 560 can be used to control the air passage so that one can admit and/or remove liquid from the tip of the outer capillary 450. The drainage of liquid should occur in a controlled way in order to maintain the optical coupling; otherwise, quick drainage of liquid from the tip of the outer capillary 450 can extinguish the resonance.

The resonator 410 of the WGM sensor 400 may be made of silica, or another glass material such as aluminosilicate and borosilicate for example. In such a case, all sorts of known surface modification established for silica and glass can be performed, including immobilization of proteins for biosensing.

As noted above, an example WGM sensor consistent with the present invention is compact, able to fit within an imaginary cylinder having a diameter of 7 mm, and even as small as 1 or 2 mm. In such example embodiments, the outer capillary (or outer tube) can be dipped into each well of a well plate easily, facilitating the use of such example WGM sensors with existing bio instruments. Indeed, such a small diameter will allow a bundle of WGM sensors to enter a well.

Mounting the resonator on a stem allows polishing the resonator's surface using a localized heat source.

In some example WGM sensors consistent with the present invention, the stem has a diameter of 300 μm to 400 μm. This provides sufficient mechanical robustness. The inventors believe that the stem diameter should be at least 30 μm in order to provide mechanical integrity. The inventors believe that a preferable stem diameter would fall in the range of 30 μm to 1 mm, and more preferably from 300 μm to 400 μm. This provides mechanical integrity while permitting a compact outer diameter of 1 mm to 2 mm.

§5.2 Example Method for Fabrication Example Sensor

An example WGM sensor, such as the one shown in FIG. 4, may be constructed in four steps—(1) fabricating the resonator and stem; (2) fabricating tapers (e.g., cones) on the feed and pickup fibers; (3) positioning the tapers relative to the resonator; and (4) attaching an outer capillary (or outer tube). Examples of how to perform each of these four steps are described in §§5.2.1-5.2.4 below.

§5.2.1 Fabrication of the Resonator and Stem

Figure 6:
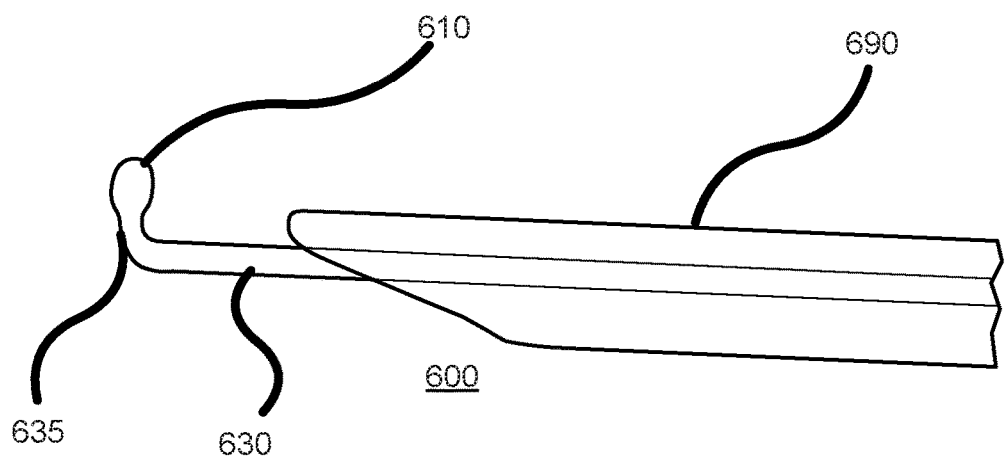
FIGS. 6-9 are microphotographs illustrating an example method for fabricating an example WGM dip sensor consistent with the present invention.

A resonator may be fabricated on a stem by first bending an optical fiber (e.g., FT400EMT, Thorlabs) at ~90° with a localized heat source such as a collimated, narrow-waist $CO_2$ laser beam, electric arc, and a microflame generated by burning $H_2$ coming out of a capillary. In one example embodiment, the bend radius was approximately 0.5 mm. Note that the smaller the bend radius, the more compact the resulting WGM sensor can be. The bent arm may then be cut to an appropriate length (e.g., ~1 mm). The tip of the bent arm (See, e.g., the bend 635 in the fiber stem 630 of FIG. 6.) may then be balled up using the same localized heat source. As shown in the microphotograph of FIG. 6, the fiber stem 620 may then be glued to the interior wall of a glass capillary 690 (e.g., inner diameter.=0.81 mm; outer diameter=1.57 mm). In the example illustrated in FIG. 6, the resonator 610 is about 4 mm away from the tip of the inner capillary 690.

§5.2.2 Fabrication of Tapers

Figure 7:
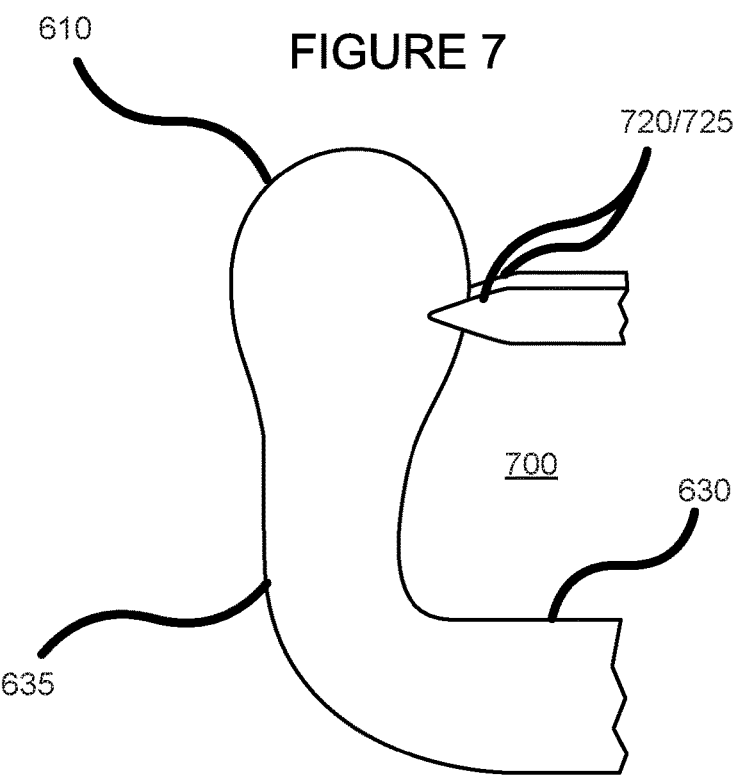

Thinned tapers less than ~4 μm in diameter are typically used to feed and pick-up light from the resonator. To eliminate (or at least reduce) the tapers' flexibility, and the resultant vulnerability of resonance to mechanical disturbances, two single mode fibers (e.g., smf28e+, Corning) may be honed into cones by etching in hydrofluoric acid solution covered with silicone oil. The fiber cones may then be glued parallel to each other. A slight convergence may facilitate introducing light into the resonator and picking up of the light. As illustrated in the microphotograph of FIG. 7, the cones of the feed and pickup fibers 720/725 in the example WGM sensor 700 do not have thinned tapers. (Compare FIGS. 11A and 11B.) The distance between the two cones can be adjusted to accommodate resonators of different diameters. As shown, the resonator 610 is attached after a bend 635 in the fiber stem 630.

§5.2.3 Positioning of Tapers Relative to the Resonator

Recall from FIG. 6 that the resonator-stem-capillary assembly 600 may be mounted on a fixed horizontal stage with the resonator 610 pointing upward. The tapers of the feed and pickup fiber assembly 720/725 may be mounted on a horizontal stage that can be moved in XYZ directions. The fiber assembly may then be moved so that the tips of the two fibers 720/725 touch the resonator 610 near its equator. This may be done by first observing them by microscope objectives, and then observing the resonance spectrum. However, the inventors learned that it is sufficient to simply position the tapers, under observation of a microscope, by the 3D positioner to slide on the outer wall of the inner capillary 690 (housing the resonator) to touch the resonator 610 near its equator. Obtaining good resonance is not difficult.

Subsequently, the fibers 720/725 may be fixed by glue 805 to the outer wall of the inner capillary 690 at the position where sharp resonance lines are observed. The inventors learned that such a construction (See, e.g., the microphotographs of FIGS. 7 and 8.) did not lose resonance when exposed to common bench-top noises. Furthermore, the inventors learned that the optical coupling (and resulting resonance) withstood disturbances caused when the WGM sensor 800 was dipped into water. However, the resonance was sometimes lost when the WGM sensor 800 was lifted from water. To prevent such a resonance loss, an outer capillary (or outer tube) may be provided. An example of providing an outer capillary is described in §5.2.4 below.

§5.2.4 Attaching an Outer Capillary (or Outer Tube)

Figure 8:
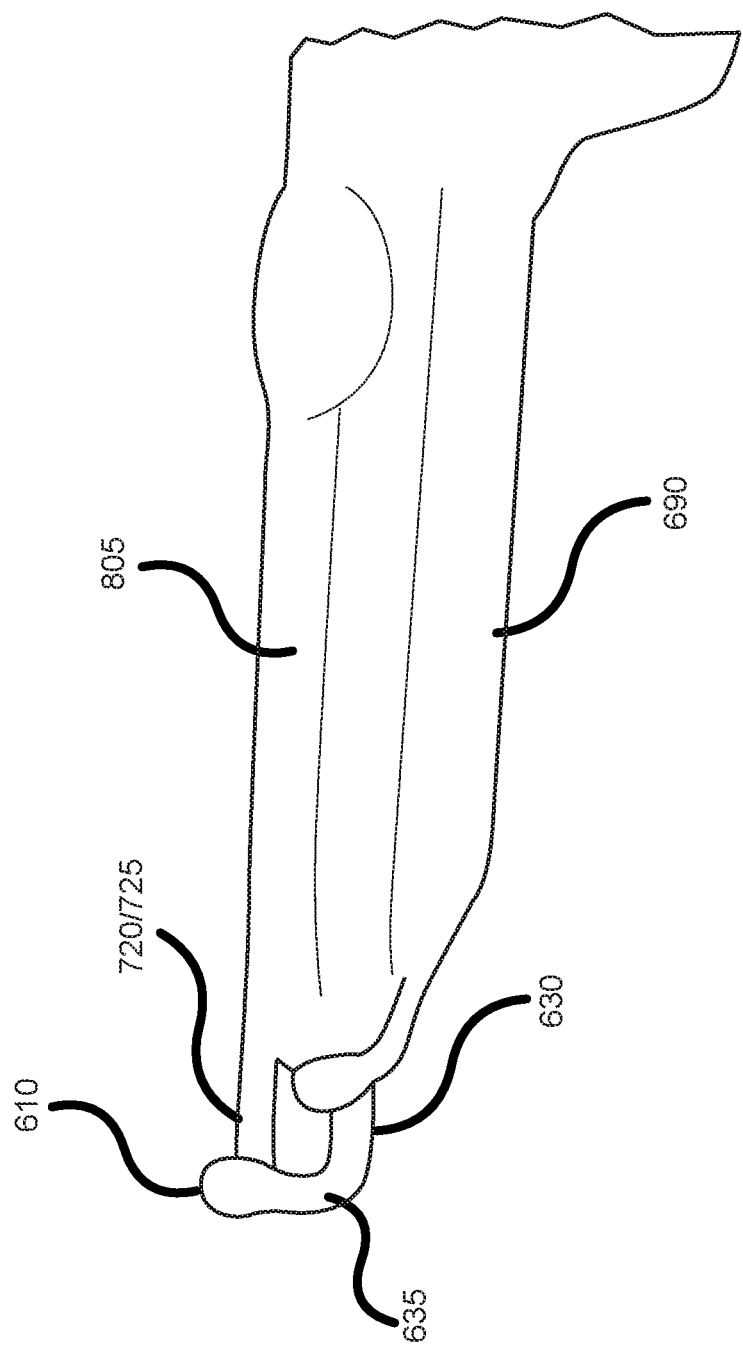
Figure 9:
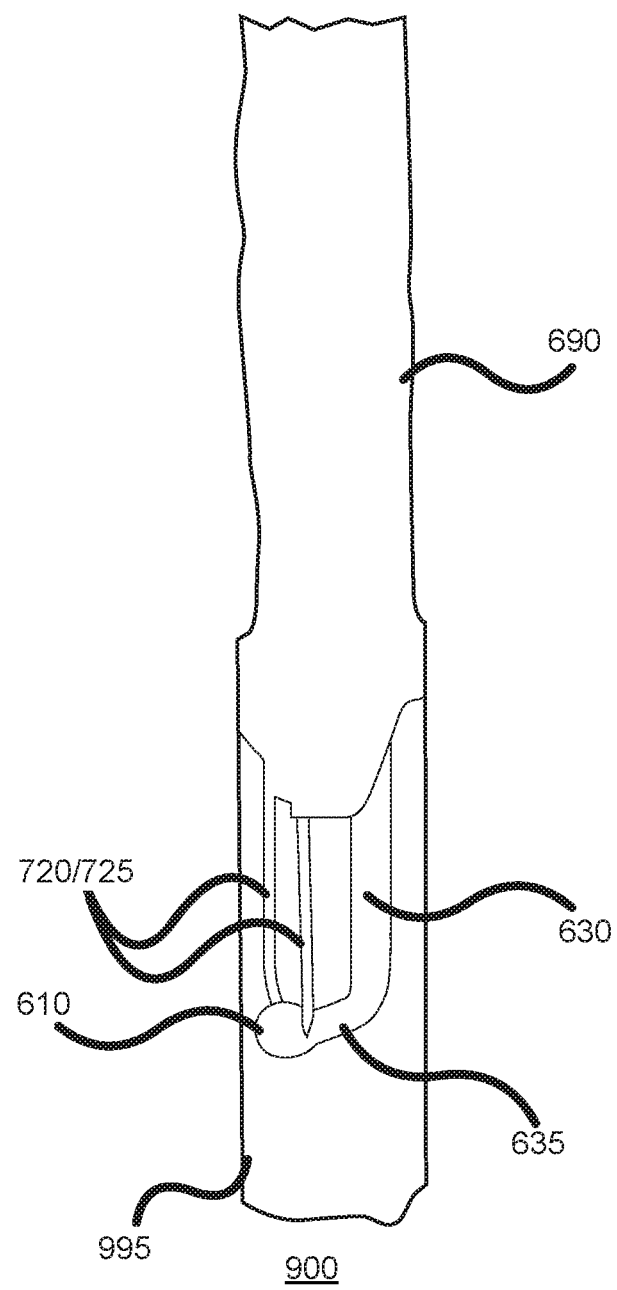

To mitigate the force experienced on the fiber-resonator assembly when this assembly 800 is lifted from water and water drains due to gravity, the fiber-resonator-stem assembly shown in FIG. 8 may be placed into a ~5 mm long outer capillary 995 (inner diameter=2.0 mm; outer diameter=2.5 mm). The resulting structure 900 is shown in the micrograph of FIG. 9. In this example WGM sensor, the distance between the tip of the fiber-resonator assembly 800 and the edge of the outer capillary 995 (i.e., the distance between the outer capillary edge and the lowest point of the resonator in the photograph below) is ~1 mm. If this distance is too small, the resonator 610 will be subject to more force when the WGM sensor 900 is dipped into, and removed from, a liquid. If, on the other hand, this distance is too large, it might take longer for the liquid being tested to displace water (or some other liquid) in the outer capillary 995 (or outer tube).

When dipped into water, the outer capillary 995 (or outer tube) is filled with water. When removed from water, most of the water was retained. In this way, the resonator 610 is always in water during lifting. As a result, forces due to lifting, which might otherwise disturb or extinguish the resonance, are reduced. This construction makes it possible to maintain the resonance during repeated dipping and lifting.

One possible disadvantage of the outer capillary 995 (or outer tube) is that when dipping the WGM sensor 900 into a solution, it takes some time for the solution to replace the liquid (or gas) within the outer capillary 995. With the example WGM sensor 900 having the dimensions listed above, the time is on the order of a minute. Referring back to FIG. 5, this rate can be controlled by controlling the size of the needle 560, and/or by controlling a pressure difference applied to the needle 560.

§5.3 Alternatives, Refinements and Extensions

Although the example embodiments described above with reference to FIGS. 4, 6, 8 and 9, used a slab or inner capillary spacer, alternative example WGM sensors consistent with the present invention do not have spacers. In one such alternative example, the acrylic coating or a jacket of the fibers would set the distance between the cones of the fibers and the stem.

Although the resonator was described as being silica, other materials for a resonator (such amorphous sapphire glass, silicon, silicon nitride, silicon oxynitride, gallium nitride (GaN), gallium arsenide (GaAs), indium arsenide (InAs), etc.) may be used in a manner consistent with the present invention.

Various chemical and biochemical processes, known to those skilled in the art, may be performed to allow the attachment of target receptors to the resonator.

In at least some exemplary embodiments consistent with the present invention, the microresonator may have a diameter of between 30 to 150 μm, though resonators having other diameters may be used.

"Target receptor" is meant to describe any bio-nanoparticle or macromolecule (e.g., virus, protein, polynucleotide, polysaccharide, etc.) that can be attached to a WGM resonator and receive a target entity of interest. Target receptors are intended to include numerous bio-nanoparticles and chemical classes, but will typically be organic molecules, or small organic compounds. Target receptors may include any functional groups (e.g., an amine, a carbonyl, a hydroxyl, a carboxyl group, sulfonyl, etc.) necessary for structural interaction (e.g., covalent bonding, hydrogen bonding, etc.) with target entities (e.g., proteins, antibodies, virus, etc.). Target receptors may include, for example, cyclical carbon or heterocyclic structures and/or aromatic or polyaromatic structures substituted with one or more of the above functional groups. Thus, target receptors may include biomolecules such as proteins, peptides, nucleic acids, saccharides, fatty acids, steroids, purines, pyrimidines, derivatives, and structural analogs or combinations thereof.

Target receptors can be obtained from a wide variety of sources including, for example, libraries of synthetic or natural compounds. Numerous means are available for random and directed synthesis of a wide variety of organic compounds and biomolecules, including expression of randomized oligonucleotides. Alternatively, libraries of natural compounds in the form of bacterial, fungal, plant and animal extracts are available to, or readily produced by, those skilled in the art. Additionally, natural or synthetically produced libraries and compounds may be modified through conventional chemical, physical and biochemical means. Known pharmacological agents may be subjected to directed or random chemical modifications, such as acylation, alkylation, esterification and/or amidification to produce structural analogs.

In some embodiments consistent with the present invention, the laser wavelength was 1070 nm, and has a laser power of between 50 μW and 50 mW, Naturally, other laser wavelengths and drive powers may be used. For example, for use in aqueous sensing, the inventors found that a 1.3 μm wavelength laser works better than a 1.5 μm wavelength laser. The inventors believe that a 1.06 μm wavelength should provide even better results, and that an 830 nm wavelength may provide still better results, provided that scattering is not too large. However, the inventors believe that further reducing the wavelength even further (for example, to 532 nm) might cause an undesirable amount of scattering.

As used in this application (and as generally understood in the art), a "protein" includes at least two covalently attached amino acids, which includes proteins, polypeptides, oligopeptides and peptides. The protein may be made up of naturally occurring amino acids and peptide bonds, or synthetic peptidomimetic structures. Thus "amino acid", or "peptide residue", as used herein means both naturally occurring and synthetic amino acids.

The target receptors may be naturally occurring proteins, or fragments of naturally occurring proteins. Thus, for example, cellular extracts containing proteins, or random or directed digests of proteinaceous cellular extracts, may be used. In this way libraries of prokaryotic and eukaryotic proteins may be made for screening in the systems described herein. Particularly preferred in this embodiment are libraries of bacterial, fungal, viral, and mammalian (e.g., human) proteins.

In at least some embodiments consistent with the present invention, the target receptors are peptides. The peptides may be digests of naturally occurring proteins as is outlined above, random peptides, or "biased" random peptides. "Randomized" means that each nucleic acid and peptide consists essentially of random nucleotides and amino acids, respectively. These random peptides (or nucleic acids) may be chemically synthesized, and therefore may incorporate any nucleotide or amino acid at any position. The synthetic process can be designed to generate randomized proteins or nucleic acids, to allow the formation of all or most of the possible combinations over the length of the sequence, thus forming a library of randomized bioactive proteinaceous agents.

In at least some embodiments consistent with the present invention, the target receptors may be nucleic acids.

"Nucleic acid" or "oligonucleotide" means at least two nucleotides covalently linked together. A nucleic acid will generally contain phosphodiester bonds, although in some cases, as outlined below, nucleic acid analogs are included that may have alternate backbones, comprising, for example, phosphoramide, phosphorothioate, phosphorodithioate, O-methylphophoroamidite, and peptide nucleic acid backbones and linkages. Other analog nucleic acids include those with positive backbones, non-ionic backbones and non-ribose backbones. Nucleic acids containing one or more carbocyclic sugars are also included within the definition of nucleic acids. The ribose-phosphate backbone may be modified to increase the stability and half-life of such molecules in physiological environments. In addition, mixtures of naturally occurring nucleic acids and analogs can be made. Alternatively, mixtures of different nucleic acid analogs, and mixtures of naturally occurring nucleic acids and analogs may be made. The nucleic acids may be single stranded or double stranded, as specified, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthanine, hypoxanthanine, isocytosine, isoguanine, and base pair analogs such as nitropyrrole and nitroindole, etc.

As described above generally for proteins, nucleic acids may be naturally occurring nucleic acids, random nucleic acids, or "biased" random nucleic acids. For example, digests of procaryotic or eukaryotic genomes may be used as is outlined above for proteins.

In general, the target receptors are designed to be complementary to a target entity, such that hybridization of the target entities and the target receptors occurs. It is not necessary for this complementarity to be perfect. For example, in the context of nucleic acid sequences, there may be one or more base pair mismatches that will interfere with hybridization between the target entity and the target receptor. However, if the number of mutations is so great that no hybridization can occur under even the least stringent of hybridization conditions, the target entity will not be considered to be complementary to the target receptor. "Substantially complementary" means that the target receptors are sufficiently complementary to the target entities to hybridize under selected reaction conditions.

In some embodiments consistent with the present invention, the target entity may be a "target sequence" which is a nucleic acid sequence on a single strand of nucleic acid. The target sequence may be a portion of a gene, a regulatory sequence, genomic DNA, cDNA, RNA including mRNA and rRNA, etc. The target sequence may be any length, with the understanding that longer sequences are more specific. As will be appreciated by those skilled in the art, the complementary target sequence may take many forms. For example, it may be contained within a larger nucleic acid sequence (e.g., all or part of a gene or mRNA, a restriction fragment of a plasmid or genomic DNA, among others.) Target receptors are made to hybridize to target sequences to determine the presence or absence of the target sequence in a sample.

In at least some embodiments consistent with the present invention, the target receptors may be organic chemical moieties.

In some embodiments consistent with the present invention, linkers may be used to attach the target receptors to the WGM resonator, to facilitate good attachment, provide sufficient flexibility to allow good interaction with the target entities, and/or to avoid undesirable binding reactions.

§5.3.1 Alternative Resonators and/or Stems

Although example embodiments consistent with the present invention describe fabricating WGM sensors using a microsphere 1010a as a resonator on a stem 1030a (See, e.g., FIG. 10A.), other resonators (such as, for example, (micro-)cylinders, (micro-)capillaries, (micro-)bubbles, (micro-)disks, (micro-)rings, (micro-)racetrack, (micro-)bottle resonator and (micro-)toroids) may be used. Referring to FIG. 10B, the resonator 1010b can be a slightly bulged cylinder arranged on a stem 1030b. The cylindrical resonator can also be supported by two fiber stems. For example, referring to FIG. 10C, an optical fiber bent twice by 90° so that the two stems 1030c are parallel to each other, and bulged at the bridge, can also be a resonator 1010c. Finally, referring to FIG. 10D, the two-sphere configuration is also possible by fusing two spheres 1010d on 90° bent stems 1030d.

§5.3.2 Alternative Attachment of Resonator to Feed and Pickup Fibers

Figure 11A:
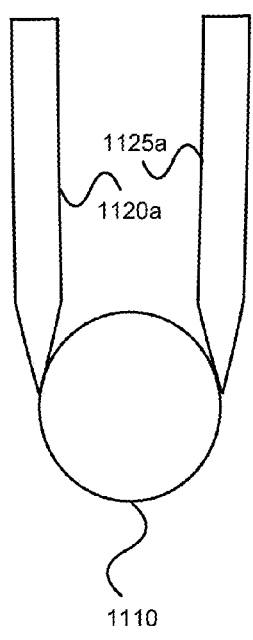
FIGS. 11A-11C illustrate alterative ways to optically (and perhaps mechanically) couple feed and pickup fibers to a resonator.
Figure 11B:
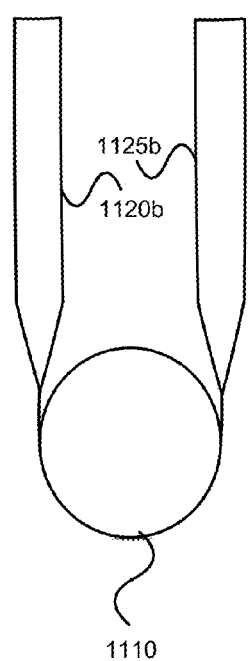
Figure 11C:
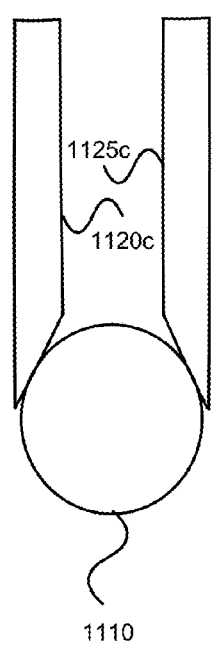

The tips of the feed and pickup fibers 1120a/1125a are not limited to cones as shown in FIG. 11A. For example, straight tapers (See 1121b and 1126b of FIG. 11B.) and angle-cut ends (See 1121c and 1126c of FIG. 11B) can also be used for the coupling with the resonator 1110. Further, although some exemplary embodiments described above used eroded optical fiber to evanescently couple light to the microresonator, other optical waveguides (such as, for example, lithographed waveguide, rib waveguides, channel waveguides, nanowires, and other structures (or media) capable of supported a guided wavemode (or of guiding electromagnetic modes) may be used instead. However, the mechanical coupling of such optical waveguides to the resonator, in concert with the mechanical coupling of the stem to the resonator, should be sufficiently robust to maintain resonance as the WGM sensor is dipped into and lifted from liquids.

Figure 12:
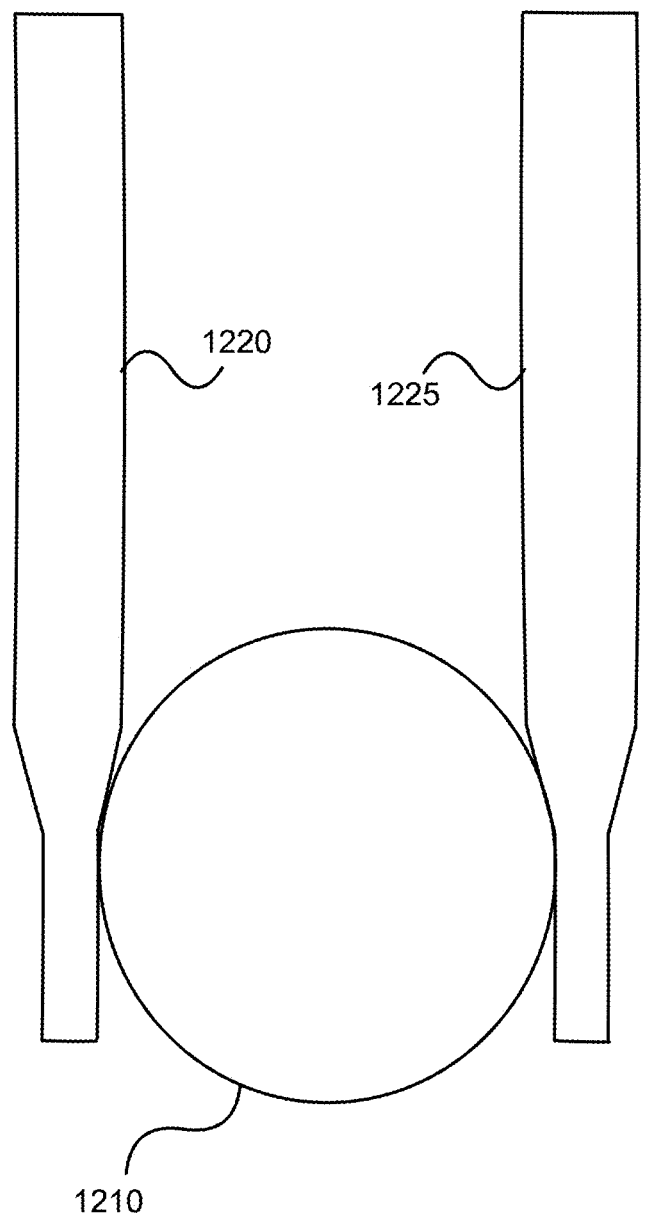
FIG. 12 illustrates an example way to optically (and perhaps mechanically) couple feed and pickup multimode fibers to a resonator.

Referring to FIG. 12, if multi-mode feed and pickup fibers 1220/1225 are used, the taper can be thick, and the resonator 1210 can touch the neck of the taper since the core is large.

§5.3.3 Alternative "King's Crown" Embodiment

Figure 13:
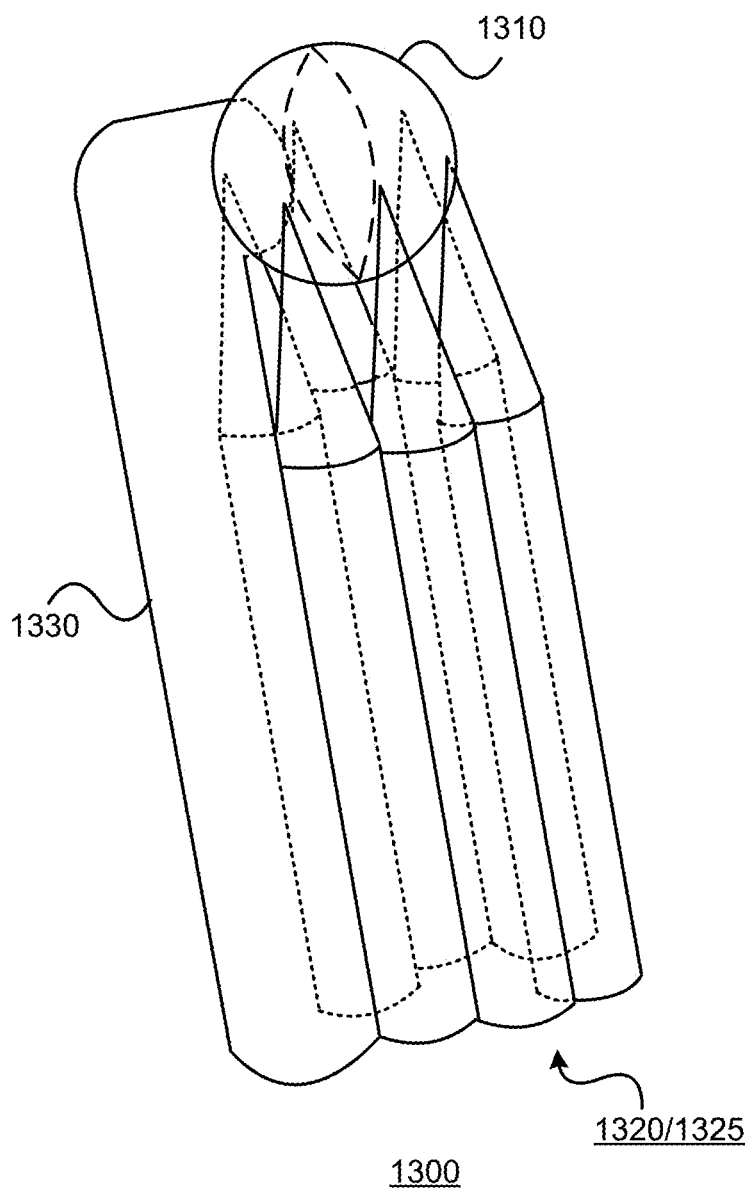
FIG. 13 is a perspective view of an example "king's crown" assembly, which may be used in a WGM sensor consistent with the present invention.

Referring to FIG. 13, another alternative WGM sensor includes a "king's crown" made from six honed fibers or tapered fibers 1320/1325 arranged in a hexagon. A 90° bent stem fiber 1330 with its tip balled up as a resonator 1310 can be positioned against the "king's crown," for example, by lining the stem 1330 along a pair of adjacent fibers that constitute part of the "king's crown." Likewise, four honed fibers can couple to a cylindrical resonator (Recall FIGS. 10B and 10C.), or a fused pair of spherical resonators (Recall FIG. 10D.).

§5.3.4 Alternative Vapor Sensing Embodiment

Figure 14:
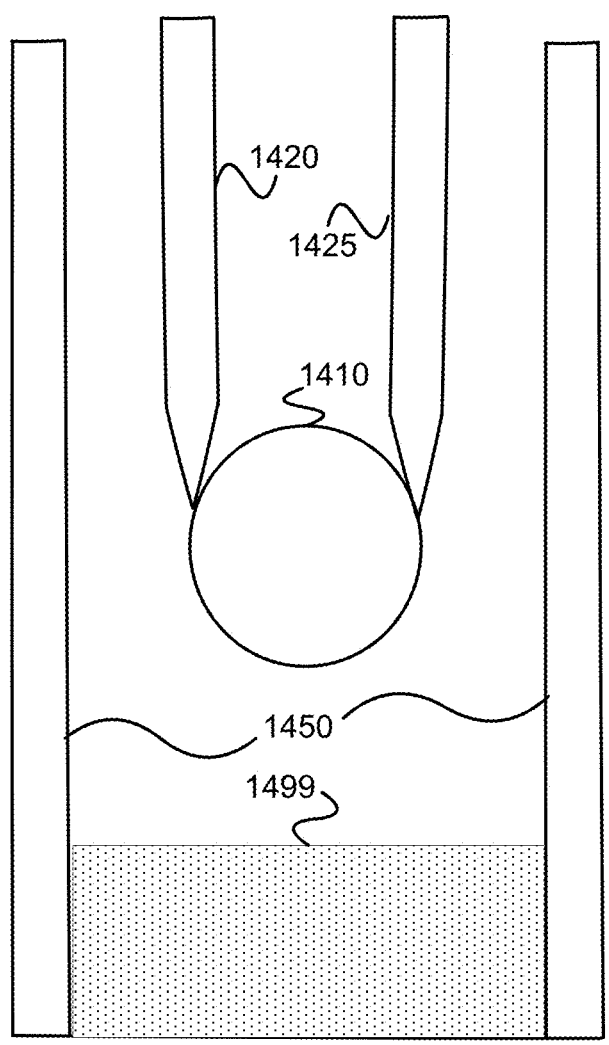
FIG. 14 illustrates an example WGM vapor sensor consistent with the present invention.

Referring to FIGS. 5 and 14, instead of providing a needle of some other air passageway (Recall FIG. 5.), in another example implementation of the WGM sensor, the glue that fixes the two fibers 1420/1425 and the resonator's stem to the interior wall of the outer capillary 1450 (or outer tube) can fill the space so that the air passage is absent. This configuration allows the resonator to be held within an air pocket when dipped into a liquid 1499. Then, some of the liquid 1499 that enters the tip of the capillary 1450 (but does not reach the resonator 1410) will vaporize to fill the air pocket with its vapor for vapor-phase sensing. The interior of the outer tubing should be chemically modified to prevent capillary rise and consequent wetting of the resonator. The liquid 1499 may also function as a conduit for volatile analyte. Since the resonator is in the vapor phase, the resonance lines are narrow (much narrower compared with those for the resonator in a liquid). Consequently, the resonator can detect a smaller shift.

§5.3.5 Alternative Including a Built in Thermistor

It is known that a temperature change of the resonator shifts the resonance wavelength as much as 10 ppm/K. The resonance wavelength is extremely sensitive to the temperature. The shift by the temperature change may well exceed the shift caused by binding of target molecules onto the resonator surface.

The present inventors found that lifting the dip sensor from an aqueous solution causes the temperature to drop, since water evaporates, depriving heat of the solution held within the tip of the dip sensor. When dipped again, the temperature rises to the original value. The present inventors also found that the temperature of the solution in a vial or well is different from that of another solution in another vial or well. Therefore it may be advisable to (1) monitor the temperature of the solution within the sensor's tip as the dip sensor moves from one solution to another and (2) remove the portion of the resonance shift due to the temperature changes from the observed resonance shift.

Figure 15:
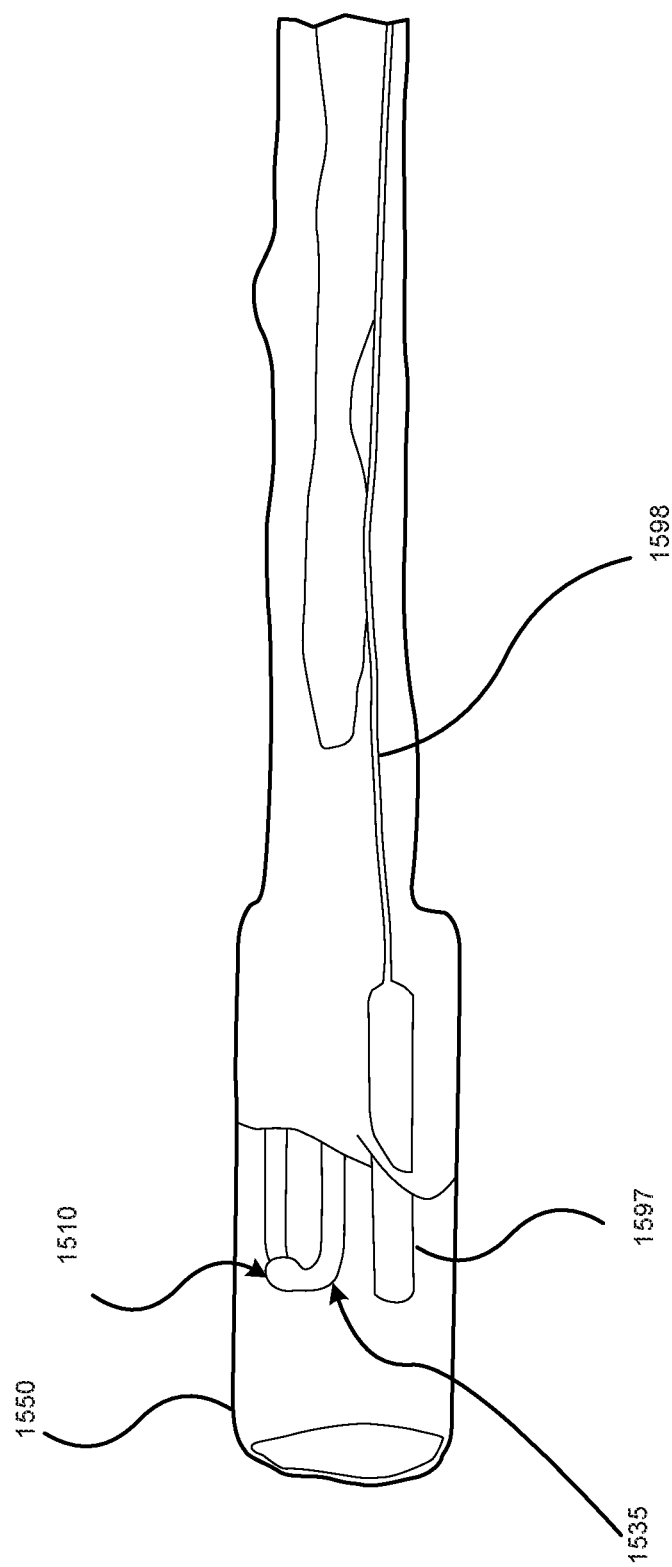
FIG. 15 is a microphotograph illustrating an example WGM dip sensor including a built in thermistor.
Figure 16:
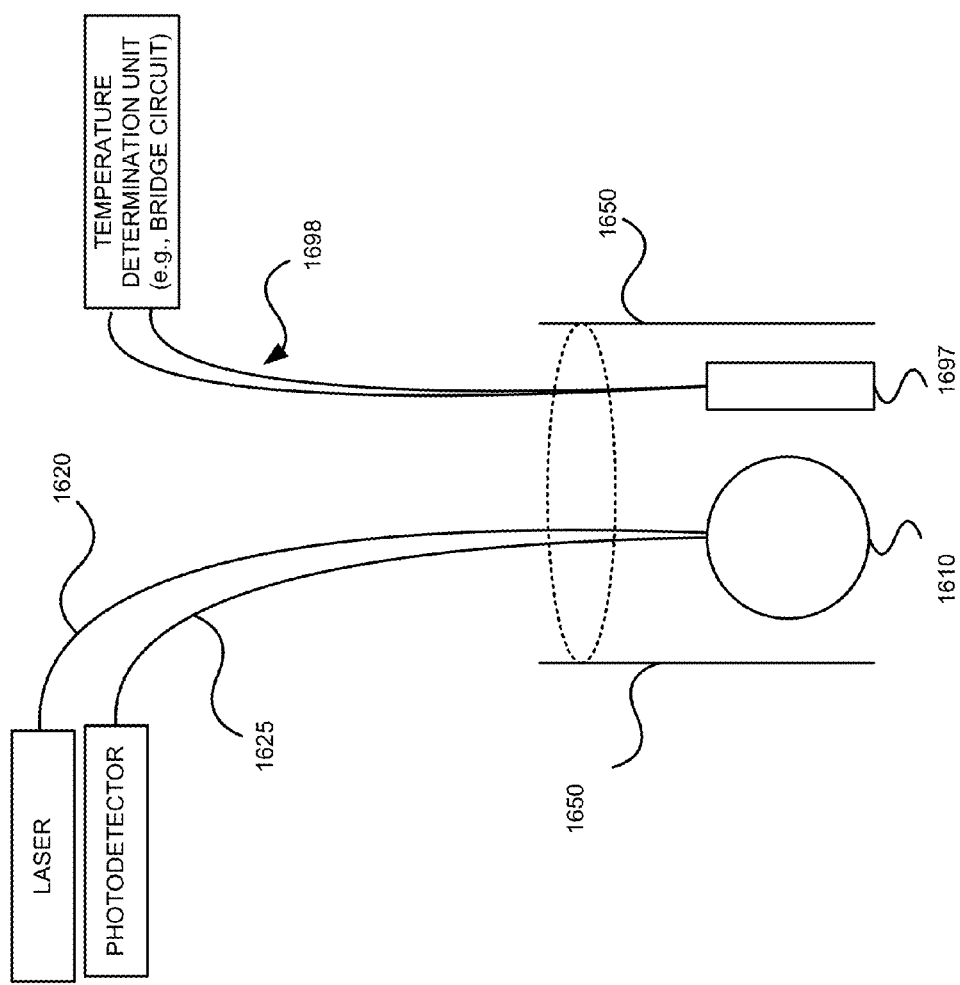
FIG. 16 is a diagram illustrating the connection of an example WGM dip sensor including a built in thermistor.

FIG. 15 is a microphotograph illustrating an example WGM dip sensor 1500 including a built in thermistor 1597. FIG. 16 is a diagram illustrating the connection of an example WGM dip sensor 1600 including a built in thermistor 1697. The resistance of the thermistor 1597/1697 may be monitored by a bridge circuit (or a high-resolution resistance meter). The sampling of the resistance value should be at least once every ten (10) seconds, and in some example embodiments, at least once every second. As shown, in one example embodiment, the thermistor 1597/1697 is provided adjacent to the resonator 1510/1610, within an outer tube 1550/1650. The bend 1535, feed fiber 1620, pickup fiber 1625, and thermistor wire(s) 1598/1698 are also shown.

§5.3.6 Refined Taper for Feed and/or Pickup Fibers

Although the example sensors 900, 1500 and 1600 of FIGS. 9, 15 and 16, respectively, include an outer tubing or outer capillary (995, 1550, and 1650, respectively), it may be beneficial to have a dip sensor that does not have an outer capillary or tubing. As noted above, the outer tube or outer capillary is provided to mechanically shield the resonator-taper assembly from the force(s) caused by fluid drainage when the assembly is lifting from the liquid well. Recall that such force(s) can cause a loss of resonance. A refined embodiment consistent with the present invention avoids an outer capillary or outer tube, while having the ability to maintain resonance through repeated dipping and lifting. Elements of such an example embodiment having a refinement to the feed and/or pickup fibers are described with reference to the microphotographs of FIGS. 17A, 17B and 18.

Figure 17B:
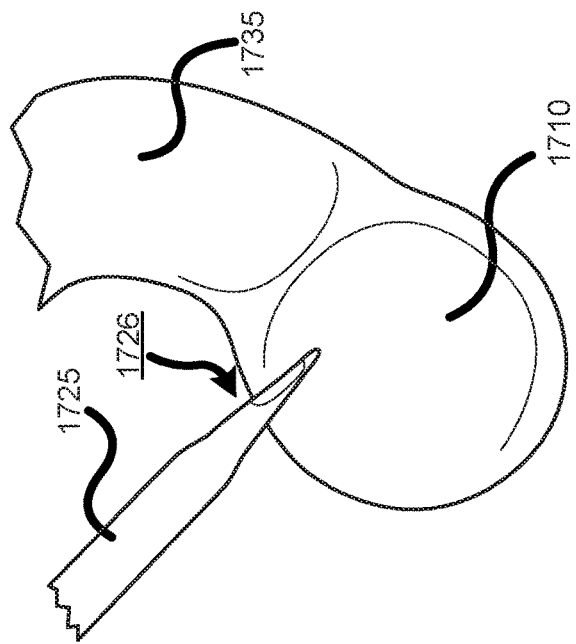
FIGS. 17A and 17B are microphotographs that illustrate elements of a sensor assembly having a refinement to the feed and/or pickup fibers.
Figure 17A:
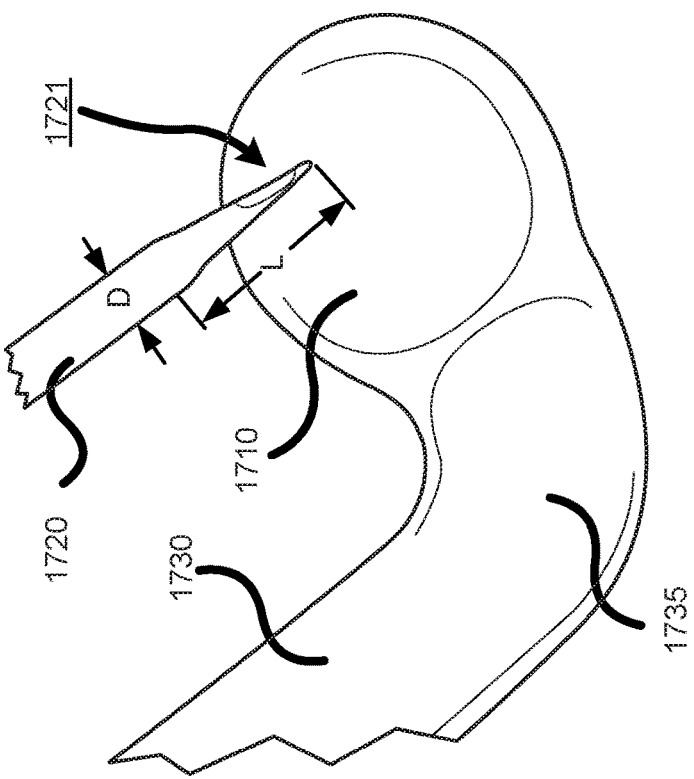
Figure 18:
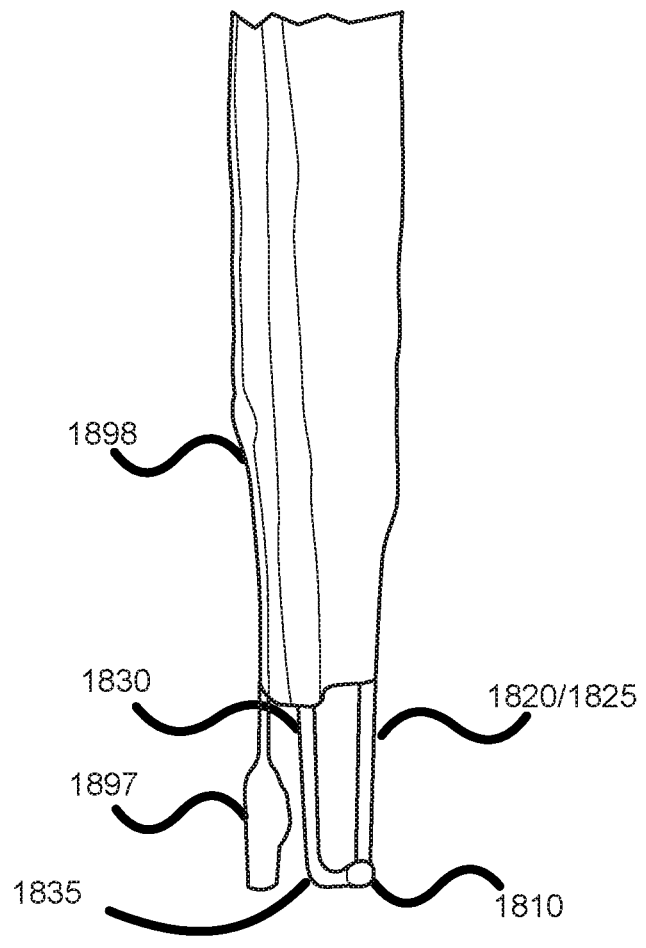
FIG. 18 is a microphotograph that illustrates elements of a sensor assembly having a refinement to the feed and/or pickup fibers.

FIGS. 17A and 17B illustrate a refinement to the tapers 1721 and 1726 of the feed and pickup fibers 1720 and 1725, respectively. As shown, the end of each of the fibers 1720/1725 is honed into a cone 1721/1726. As shown in FIG. 17A, the distance (L) between the tip of the cone 1721 and the base of the cone 1721 (where the base is as thick as the feed fiber 1720) is 2 to 10 times as large as the diameter (D) (e.g., D=125 μm) of the feed fiber 1720. Although not shown in FIG. 17B, length of the cone 1726 to the diameter of the pickup fiber 1725 has the same relationship as that in the feed fiber 1720. The microsphere resonator 1710 and the bend 1735 of the stem 1730 are also shown. Note also that the cones 1721/1726 are offset from an equator of the microsphere 1710. The inventors found that with the foregoing cone geometry, the assembly can maintain resonance in repeated dipping and lifting, even without an outer capillary or tube. FIG. 18 is a microphotograph depicting an embodiment 1800 including a resonator 1810 attached to a stem 1830 at a bend 1835, and attached to the feed and pickup fibers 1820/1825. A thermistor 1897 and thermistor wires 1898 are also shown.

The present inventors believe that the smaller angle (sharper tip) of the cones 1721/1726 allows a larger area of contact between the side of the cones 1721/1726 and the resonator 1710, thereby enhancing the mechanical support of the resonator 1710. The inventors believe that the light transmitted through the feed fiber 1720 and the cone 1721 does not transfer to the resonator 1710 through this mechanical contact. Rather, the inventors believe that the light is transferred to the resonator 1710 from the tip of the cone 1721 across a gap to the resonator 1710. This is in contrast to a design having a cone with a lower length to diameter ratio (e.g., 1.5) (referred to as a "blunt cone" design). In such a blunt cone, the blunt tip of the cone might require it to both (1) mechanically support the resonator and (2) couple light between the cone and the resonator. To make the coupling weak, the area of contact in the coupling in such a blunt cone is held small, which may compromise the mechanical support.

The refined cone design enhances the mechanical support, and the provision of an outer capillary or tube can therefore be avoided. Consequently, the diameter of the dip sensor 1800 can be made less than those (Recall, e.g., 900, 1500 and 1600) with the outer capillary or tubing. Since eliminating the outer capillary or tubing also reduces the time for fluid entering and exiting a region proximal to the resonator 1810 for sensing (and for targets to diffuse to this region), the time required for sensing should also be reduced relative to the example embodiments having an outer capillary or tubing.

§6. CONCLUSIONS

Example embodiments consistent with the present invention enable people who have not been trained in photonics to use a WGM sensor for dip sensing and/or vapor sensing. Such example WGM sensors have many useful applications, for example, in clinical diagnostics, screening of cows for BSE (to replace ELISA), chemical analysis (in QA/QC, for example), etc. The surface of the resonator can be modified to each user's own need, for example, attaching an antibody for detecting an antigen.

Since example WGM sensors consistent with the present invention use light guided by optical fibers and a submillimeter resonator, they can be more compact than other high sensitivity sensing methods. For example, compared with sensors using a fluidic device, a much smaller volume of the sample solution required. If the solution is provided in a well (e.g., of a well plate), the solution within the well is ready for the next sensing (by a different type of probe) when the WGM sensor assembly is lifted.

Example WGM dip sensors consistent with the present invention may be incorporated into standard liquid-handling instruments that use well plates, which are widely used in biology and clinical labs.

Apart from dip and vapor sensing, example WGM sensors consistent with the present invention may be used in devices (such as telecommunications devices for example) to process optical signals (for example, to provide a wavelength filter that may replace a Bragg fiber grating in telecom applications). Indeed, embodiments consistent with the present invention include any assembly including (a) a stem; (b) a whispering gallery mode ("WGM") resonator mechanically supported by the stem; (c) feed and pickup optical fibers optically coupled with the WGM resonator and mechanically coupled with the stem, thereby defining a stem-resonator-fiber assembly. A portion of such a stem-resonator-fiber assembly including the WGM resonator can fit within an imaginary cylinder having a diameter of 7 mm. In other example embodiments consistent with the present invention, the diameter of the imaginary cylinder is 2 mm. In still other example embodiments consistent with the present invention, the diameter of the imaginary cylinder is 1 mm.

What is claimed is:

1. Apparatus comprising:
   a) a stem;
   b) a whispering gallery mode ("WGM") resonator mechanically supported by the stem; and
   c) feed and pickup optical fibers optically coupled with the WGM resonator and mechanically coupled with the stem, thereby defining a stem-resonator-fiber assembly, wherein a portion of the stem-resonator-fiber assembly including the WGM resonator can fit within an imaginary cylinder having a diameter of 7 mm, and wherein the portion of the feed and optical pickup fibers that can fit within the imaginary cylinder is longer than the diameter of the imaginary cylinder.

2. The apparatus of claim 1 wherein the portion of the stem-resonator-fiber assembly including the WGM resonator can fit within an imaginary cylinder having a diameter of 2 mm.

3. The apparatus of claim 1 wherein the portion of the stem-resonator-fiber assembly including the WGM resonator can fit within an imaginary cylinder having a diameter of 1 mm.

4. The apparatus of claim 1 wherein the mechanical support of the WGM resonator by the stem and the mechanical coupling of the feed and pickup optical fibers with the stem is such that the resonator can be dipped into and removed from a liquid contained in a well having a diameter of less than 7 mm while maintaining a WGM resonance in the WGM resonator.

5. The apparatus of claim 1 wherein the stem includes a bend of approximately 90 degrees.

6. The apparatus of claim 1 wherein the feed and pickup optical fibers physically contact the WGM resonator.

7. Apparatus comprising:
   a) a stem;
   b) a whispering gallery mode ("WGM") resonator mechanically supported by the stem; and
   c) feed and pickup optical fibers optically coupled with the WGM resonator and mechanically coupled with the stem, thereby defining a stem-resonator-fiber assembly, wherein a portion of the stem-resonator-fiber assembly including the WGM resonator can fit within an imaginary cylinder having a diameter of 7 mm, and wherein the feed and pickup optical fibers are mechanically coupled with the stem via a spacer.

8. The apparatus of claim 7 wherein the spacer is defined by an outer wall of an inner capillary.

9. The apparatus of claim 1 further comprising:
   d) an outer capillary defining an inner volume accommodating the WGM resonator.

10. The apparatus of claim 9 further comprising:
    e) a thermistor provided within the outer capillary.

11. The apparatus of claim 9 wherein an air passage is defined from a first open end of the outer capillary to an outlet in the outer capillary.

12. The apparatus of claim 11 wherein the air passage is defined by a hollow needle.

13. The apparatus of claim 1 wherein the feed optical includes a conical distal end mechanically and optically coupled with the WGM resonator at a first location on the WGM resonator,
    wherein the pickup optical fiber includes a conical distal end mechanically and optically coupled with the WGM resonator at a second location, different from the first location, on the WGM resonator, and
    wherein the feed and pickup optical fibers extend in parallel directions.

14. The apparatus of claim 1 wherein the WGM sensor is a sphere.

15. The apparatus of claim 1 wherein the WGM sensor is a cylinder.

16. The apparatus of claim 1 wherein the stem has a diameter of at least 30 μm.

17. The apparatus of claim 1 wherein the stem has a diameter of from 300 μm to 400 μm.

18. The apparatus of claim 1 wherein the stem has a diameter of from 30 μm to 1 mm.

19. The apparatus of claim 1 further comprising a thermistor arranged proximal to the WGM resonator.

20. The apparatus of claim 1 wherein at least one of the feed and pickup optical fibers is optically coupled with the WGM resonator via a cone at its end, and wherein a distance between a tip of the cone and a base of the cone is 2 to 10 times as large as a diameter of the optical fiber.

21. Apparatus comprising:
    a) a stem;
    b) a whispering gallery mode ("WGM") resonator mechanically supported by the stem; and
    c) feed and pickup optical fibers optically coupled with the WGM resonator and mechanically coupled with the stem, thereby defining a stem-resonator-fiber assembly, wherein a portion of the stem-resonator-fiber assembly including the WGM resonator can fit within an imaginary cylinder having a diameter of 7 mm, and wherein each of the feed and pickup optical fibers includes a conical distal end mechanically and optically coupled with the WGM resonator.

* * * * *

UNITED STATES PATENT AND TRADEMARK OFFICE
CERTIFICATE OF CORRECTION

PATENT NO. : 9,804,331 B2
APPLICATION NO. : 14/823840
DATED : October 31, 2017
INVENTOR(S) : Monica Agarwal, Natalie Huiyi Luo and Iwao Teraoka Page 1 of 1

It is certified that error appears in the above-identified patent and that said Letters Patent is hereby corrected as shown below:

In the Specification

Column 1, Line 33:
Replace: "This invention was made with Government support and the Government may have certain rights in the invention as provided for by grant number 1040015 awarded by the National Science Foundation."
With: -- This invention was made with government support under grant number 1040015 awarded by the National Science Foundation. The government has certain rights in the invention. --

Signed and Sealed this
Thirtieth Day of April, 2019

Andrei Iancu
*Director of the United States Patent and Trademark Office*